United States Patent
Davalli et al.

(10) Patent No.: US 6,740,123 B2
(45) Date of Patent: May 25, 2004

(54) SYSTEM FOR THE CONTROL AND MONITORING OF FUNCTIONAL DEVICE FOR THE DISABLED WITH ENERGY FROM OUTSIDE THE BODY AND A METHOD FOR THE REMOTE CONTROL THEREOF

(75) Inventors: Angelo Davalli, Budrio (IT); Rinaldo Sacchetti, Nova Feltria (IT)

(73) Assignee: I.N.A.I.L. Centro per la Sperimentazione Ed Applicazione di Protesi e Presidi Ortopedici per Gli Infortuni Sul Lavoro, Bologna (IT)

( * ) Notice: Subject to any disclaimer, the term of this patent is extended or adjusted under 35 U.S.C. 154(b) by 155 days.

(21) Appl. No.: 10/032,059

(22) Filed: Dec. 31, 2001

(65) Prior Publication Data
US 2002/0143405 A1 Oct. 3, 2002

(30) Foreign Application Priority Data
Mar. 30, 2001 (EP) .............................. 01830226

(51) Int. Cl.$^7$ ................................. A61F 1/00
(52) U.S. Cl. .............................. 623/24; 623/25; 623/57
(58) Field of Search .................. 623/24, 25, 57–65; 700/245, 249

(56) References Cited

U.S. PATENT DOCUMENTS

| | | |
|---|---|---|
| 4,030,141 A | 6/1977 | Graupe |
| 4,209,860 A | 7/1980 | Graupe |
| 4,314,379 A | 2/1982 | Tanie et al. |
| 4,580,569 A | 4/1986 | Petrofsky |
| 5,336,269 A | 8/1994 | Smits |
| 5,413,611 A | 5/1995 | Haslam, II et al. |

FOREIGN PATENT DOCUMENTS

| | | |
|---|---|---|
| DE | 15 41 299 A | 7/1969 |
| FR | 2509603 A | 1/1983 |

OTHER PUBLICATIONS

Kitzenmaier P et al. "Möglichkeiten der myoelecktrischen Ansteuerung von Gliedmassenprotesen" Biomedizinische Technik, Fachverlag Schiele Und Schoen GMBH. Jul. 1, 1992, pp. 170–180, vol. 37., No. 7/8, ISSN: 0013–5585, Berlin DE.

Hudgins et al, "A new strategy for Multifunction Myoelectric Control" IEEE Transactions on Biomedical Engineering, vol. 40, No.: 1, Jan. 1983 PP 82–94.

*Primary Examiner*—David O. Reip
(74) *Attorney, Agent, or Firm*—Sughrue Mion, PLLC

(57) ABSTRACT

The present invention relates to a system for the control and monitoring of functional devices for the disabled with energy from outside the body, comprising actuator element(s), data-processing element(s), and control element(s) connected to the actuator element(s) to the processing element(s). The system further comprises a sensor element which is connected to the control element(s) and can transmit one or more signals for the control and monitoring of functional devices for the disabled. The present invention also relates to the procedures necessary for the remote control and monitoring of the system.

14 Claims, 4 Drawing Sheets

SYSTEM FOR THE CONTROL AND MONITORING OF FUNCTIONAL DEVICE FOR THE DISABLED WITH ENERGY FROM OUTSIDE THE BODY AND A METHOD FOR THE REMOTE CONTROL THEREOF

BACKGROUND OF THE INVENTION

The present invention relates to the field of functional devices for the disabled and, in particular, but not exclusively, to a system for the control and monitoring of functional upper-limb prostheses with energy from outside the body. The present invention also relates to a method for the remote control of a system of this type.

In recent years, progress in electronics has also given a technological boost to the field of devices for the disabled. Reference is made in particular to biotechnological devices, to carriages, and to prostheses with a high technological content, in which the presence of sensors and of electronic components improves the performance of the device.

The upper-limb prosthesis is certainly one of the functional devices for the disabled which presents the greatest technological problems in its construction and control. In particular, the provision of a prosthetic hand is particularly difficult because of aspects connected both with aesthetics and with functionality, as; well as with the actual degree of complexity of this member.

A human being's upper limb is used not only for its gripping capability, but often as a means of indirect or direct communication, for example, in people who suffer from a speech defect, or for assessing the nature, consistency and physical characteristics of an object by means of sensory receptors of various kinds, Owing to this complexity, there are many known solutions for upper-limb prostheses which differ from one another according to their functional characteristics and to the type of energy used for their operation. In particular, it is possible to distinguish between passive prostheses, amongst which are cosmetic, operative, exoskeletal or endoskeletal prostheses, and active prostheses, amongst which are those using body energy, those using energy from outside the body, and those with myoelectrical or electronic control.

An active upper-limb prosthesis with energy from outside the body uses energy supplied by a storage device to drive one or more direct-current electric motors the movement of which brings about closure or opening of an artificial hand, flexion-extension of an artificial elbow, and pronation-supination of an artificial wrist of the prosthesis. These prostheses are divided further into myoelectrical and electronic prostheses according to the type of control source used, that is, according to the type of sensor.

Myoelectrically-controlled prostheses use as sensors surface electrodes which are placed in contact with the skin of the natural limb and can detect an electromyographic signal generated as a result of an isometric contraction of the underlying muscles. This signal, which arises from the intrinsic contraction mechanism of the muscle fibre, has a very low value such that it has to be reprocessed to produce a significant signal for the control circuits of the prosthesis. A necessary condition in order to be able to use signals of this type is that they must have an amplitude such as to be recognized by the sensor and that they must be capable of being generated independently of one another.

SUMMARY OF THE INVENTION

In the field of functional devices for the disabled, developments in mechanical and electronic technology have led to the use of ever more sophisticated and complex technological components in order to achieve results as similar as possible to those of a natural limb. This increase in complexity has created the need for ever more rapid and precise management of the control parameters of the prosthetic devices, making it necessary to back them up with microprocessor circuits.

Another problem resulting from these recent developments is connected with pre-setting, calibration, and resolution of breakdowns in devices of this type, requiring skilled personnel and specialized equipment which are often difficult to find in the field.

The object of the present invention is to provide a system for the control, monitoring and management of functional devices for the disabled with energy from outside the body and, in particular, of upper-limb prostheses, which solves the above-mentioned problems.

Another object is to provide a method for the remote control and management of devices of this type, both for periodic maintenance and in the event of unexpected breakdown or malfunction.

A further object of the present invention is to provide a functional device for the disabled which is safe and reliable, which can be maintained quickly, and which can easily be adapted to the specific requirements of each individual patient.

To achieve the objects indicated above, the subject of the invention is a system for the control and monitoring of functional devices for the disabled with energy from outside the body, and a method for the remote control thereof, as defined in the appended claims.

In a particular embodiment of the present invention, a functional device for the disabled comprises a microprocessor electronic-control element which acquires surface electrical potentials generated by the contraction of the muscles, using them, after a processing stage, as signals for the control of the prosthesis, and controlling a plurality of drive means, for example, but not exclusively, direct-current motors.

One of the main advantages of the present invention is that the number of signals input to the control element can be minimized, when required, without thereby reducing the capabilities and the management characteristics.

Another advantage of the present invention consists of the use of skin electrodes for detecting surface electrical potentials, since they can be fitted on the patient without surgical operations, and maintenance operations can be minimized. Moreover, the technical characteristics of these electrodes enable a slowly variable and rectified signal to be produced, which can easily be converted into a digital quantity.

In one embodiment of the present invention, the signals are processed by a micro control unit (an MCU) which can detect the stimuli, operate the motors, and check that the circuits and the motors are not subject to operating parameters greater than their specifications. The MCU recognizes three families of signals: that of signals which are generated by the patient's muscles and are devoted to bringing about a movement, that of muscle signals which are devoted to selecting the function to be selected, and that of signals which are generated by the motors or by the sensors and are devoted to protecting the prosthesis.

The use of a processor (an MCU) also enables the principle functions performed by the functional device for the disabled to be implemented by means of programming codes so that it is not necessary to operate on electronic circuits and there is no need to design an individual electronic circuit for each different function. The adoption of these characteristics is also particularly advantageous in terms of saving of time at the stages of the production of prototypes and the pre-setting and calibration of the device.

A further advantage of the present invention is that it allows for maximum adaptability of the control element to very varied patients' needs by the definition of a set of operative parameters at the fitting and training stage so as to render the use of the functional device as direct and natural as possible.

In a particular embodiment of the present invention, an 8-bit MCU with integrated peripherals has been selected so as to minimize size and the consumption of energy by the control system for given functions implemented.

Another important characteristic of the present invention is the adoption of a motor brake element, for example, but not exclusively, an electronic brake element, for keeping the various drive means in position in the absence of stimuli from the skin electrodes. When a patient provided with an electromechanical elbow is carrying a load or sets the position of any portion of the functional device, the position is thus maintained, even after external stresses, without the system having to make an active compensation effort.

In order to maintain a high degree of safety and reliability, the functional device of the present invention also comprises means for preventing excessive electrical stresses on the drive means and on the electronic circuitry. For example, but not exclusively, the MCU comprises an ADC port which constantly monitors current consumption by means of a particular integrated circuit, converting the measurement of current absorbed by the supply to a proportional voltage level. When the voltage exceeds normal operating levels for a period of time greater than a predetermined period, the processor stops the drive means and waits for the patient's muscles to relax. One embodiment of the present invention also comprises means for detecting the travel limits of the various portions of the functional device so as to prevent wear or breakage of the mechanical and/or electronic components.

BRIEF DESCRIPTION OF THE DRAWINGS

The control and monitoring system of the present invention also comprises a method for the communication of data between the MCU and an external processor so as to permit two-way communication of the necessary information. Configuration data and operating parameters can be transmitted to the control element and are stored in data-storage elements, for example, but not necessarily, non-volatile EEPROM memories, so as to enable the functional device to operate normally even in the absence of communication with external data sources. Data relating to the operation of the control element, for example, the set of parameters used and the data input to the ADCs, can be transmitted to the external processor for graphic display.

The above-mentioned system also comprises expansion means for the electronic circuits and for the drive means such as, for example, but not exclusively, eccentric motors for indicating emergency situations, for example, by means of vibrations, and for the data-communication means such as, for example, but not exclusively, communication ports compatible with the I²C protocol, EEPROM memories, sensors and RAM memories.

Figure 1:
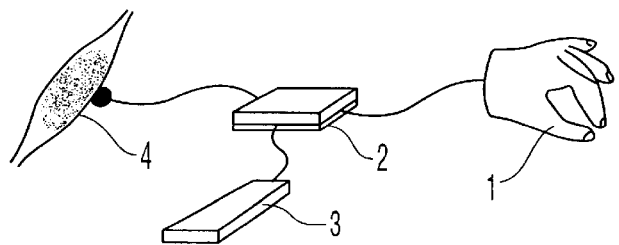
Figure 2:
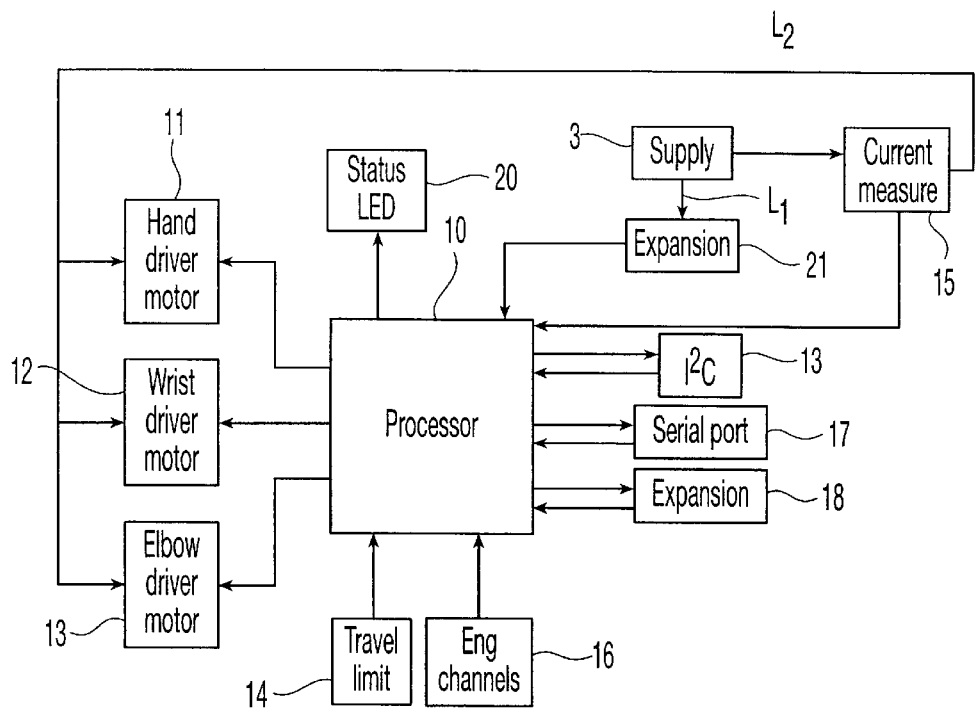
Figure 3A:
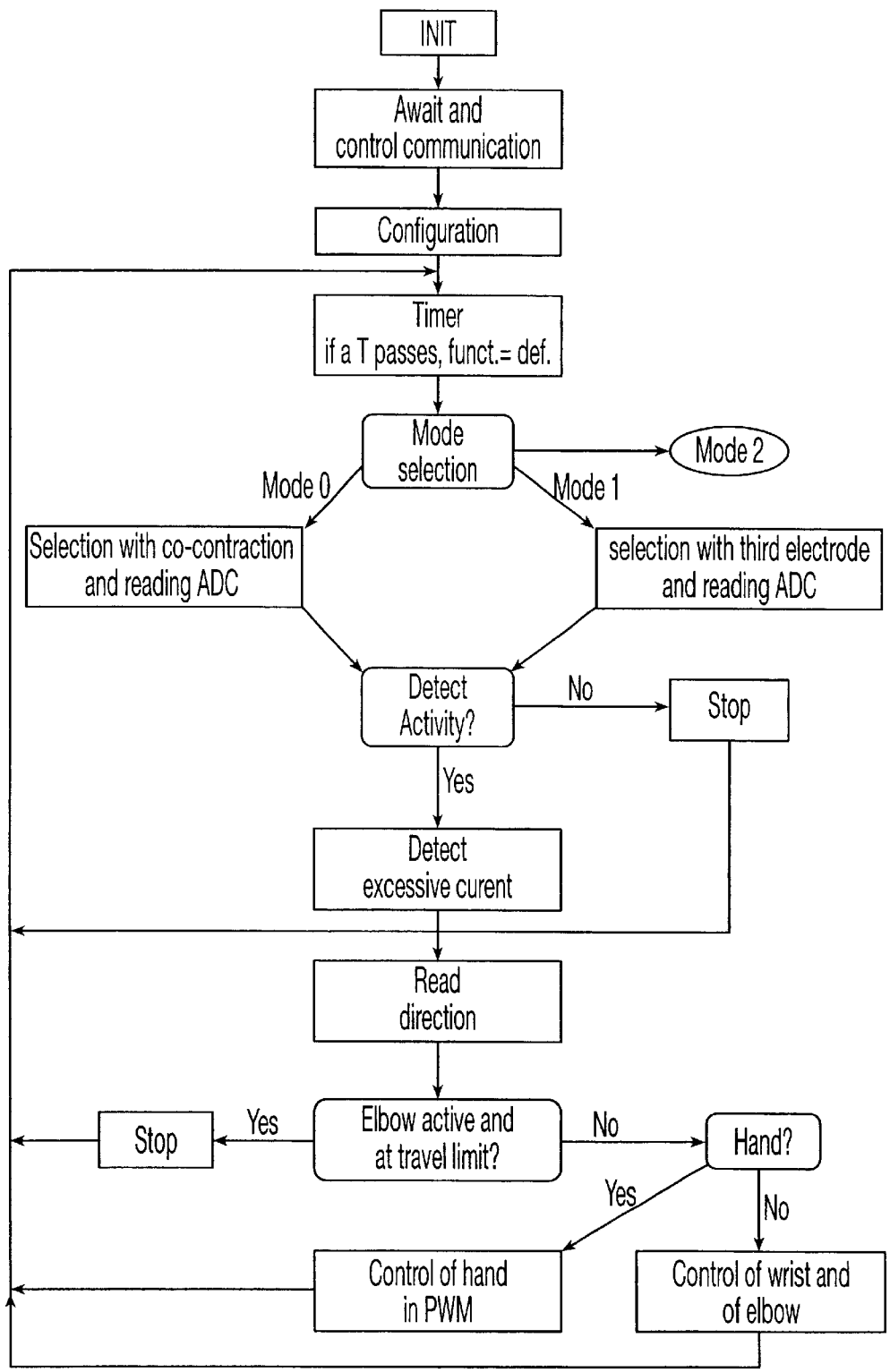
Figure 3B:
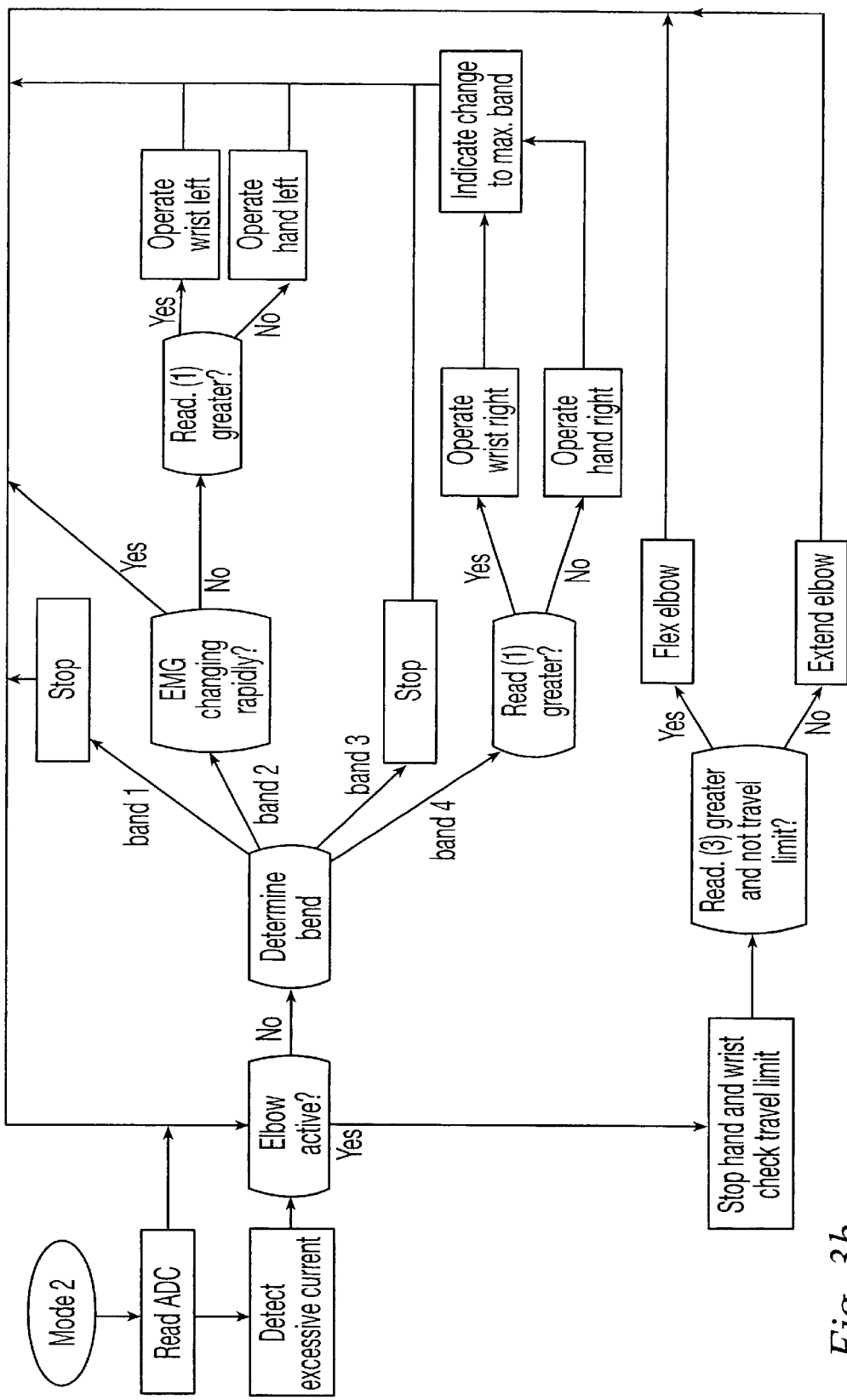
Figure 4:
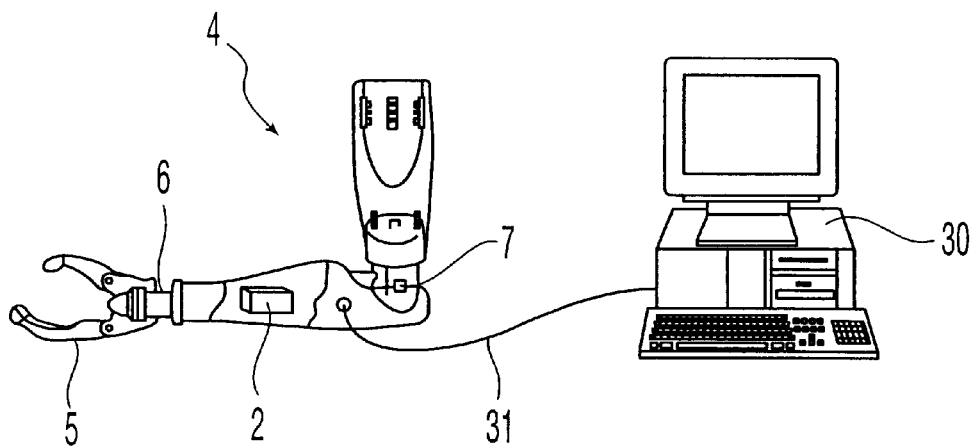
Figure 5:
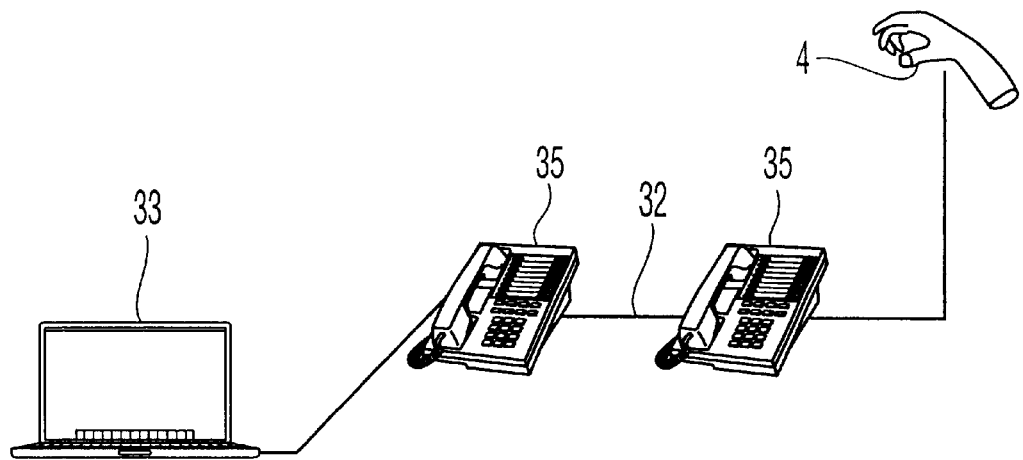

Further characteristics and advantages will become clear from the following detailed description of an embodiment of the invention, given with reference to the appended drawings, provided purely by way of non-limiting example, in which:

FIG. 1 is a schematic view of a system for the control and monitoring of functional devices for the disabled with energy from outside the body, according to the present invention, FIG. 2 is a block diagram of a control element of the system shown in FIG. 1, FIGS. 3a and 3b show a schematic flow chart of the method for the control of a functional device for the disabled, FIG. 4 is a schematic view of the interface between a functional device of the present invention and an external processor, and FIG. 5 is a schematic view of a remote-control system for a functional device for the disabled.

DETAILED DESCRIPTION OF THE INVENTION

With reference now to the drawings, a functional device for the disabled with energy from outside the body according to the present invention comprises an active functional prosthesis, for example, but in non-limiting manner, an upper-limb prosthesis 1 of known type, means 4 for detecting electromyographic signals, a control element 2, and a supply 3 which supplies energy to the functional prosthesis 1, to the control element 2, and to the sensors present. The functional prosthesis 1 comprises drive means, for example, direct-current electric motors, resilient means, and mechanical components which, in combination with one another, perform the function of an artificial hand 5, wrist 6, and elbow 7. Since this prosthesis is of known type, it will not be described in detail in the following description.

Owing to the different requirements of the functional prosthesis 1 and of the control element 2 with regard to voltage level and stability and to electrical-current absorption, it is necessary to differentiate the distribution of electric current by the supply 3, for example, but in non-limiting manner, by means of a regulator element producing, for example, a line with about 5V and 100 mA for the electronic circuits and a line with about 7.5 V and 3 A for the functional prosthesis 1. In one embodiment of the present invention, the control element 2 also includes the supply 3.

FIG. 2 is a block diagram of the control element 2, comprising a processor 10 of a known type easily obtainable commercially. Many tests carried out by the Applicant have identified, amongst the various processor models which satisfy the requirements and the specifications of the system, the processor PICMicro 16F87x. The processor 10 has outputs connected to actuator means 11, 12, 13 for drive means (not shown) of the functional prosthesis 1, and inputs connected to a travel-limit detector 14, to a current measurer 15, and to electromyographic signal-transmission means 16, to which means for detecting electromyographic signals, for example, but in non-limiting manner, skin electrodes 4 for detecting the surface electrical potentials of a patient's skin, are connected. The processor 10 also has bidirectional connections to a serial port 17, to an expansion connector 18, and to an I²C port 19 for connection to further peripheral devices.

The actuator means 11, 12 and 13 are controlled by TTL levels coming from the processor 10 and enable the direct-current motors of the hand 5, of the wrist 6, and of the elbow 7 of the functional prosthesis 1, respectively, to be controlled. Different solutions have been selected for the construction of the actuator means 11, 12 and 13, according to the motor concerned, since the power absorbed and, above all, the peak current requirements are different. It is in fact necessary to bear in mind the different uses of the portions of the functional prosthesis 1; since the elbow 7 is used to lift objects and thus to develop a force of some magnitude, the power circuitry of the elbow 7 must have dimensions such as to provide sufficient current for prolonged periods of time without dissipating excessive heat, which could be dangerous; in contrast, the hand and wrist portions 5 and 6 of the functional prosthesis 1, which are responsible for manipulation, do not have to make large efforts and do not therefore require high electrical power. On the basis of these considerations, an embodiment of the present invention comprises, for example, but not exclusively, H-shaped bridge circuits of known type, formed by elements incorporated in the actuator means 11 and 12 for the wrist 6 and the hand 5, respectively, and by discrete elements in the actuator means 13 for the elbow 7 of the functional prosthesis 1.

The travel-limit detector 14 detects the reaching of maximum flexion by the elbow 7 of the functional prosthesis 1 and indicates this, by means of a low logic level, to the processor 3, which acts accordingly. In particular, when the maximum flexion of the elbow 7 is reached, persistence of the flexion command generates a very large effort which leads to a peak of current absorbed. This large rise in electrical current is detected by the processor which deactivates the drive means, thus making use of a feature already implemented, without further complicating the circuitry. During the extension movement, however, it is not possible to make use of this method since the elbow 7 of the functional prosthesis 1 contains a joint-release mechanism which is activated when the joint reaches the point of maximum extension. The adoption of this mechanism was rendered necessary to enable the elbow 7 of the functional prosthesis 1 to engage in a swinging movement when the patient is walking. The travel limit during the extension movement is therefore indicated by the pressing of a switch disposed on the elbow 7 of the functional prosthesis 1, slightly before the position of maximum extension is reached. The processor 10 continuously reads the digital signal generated by this switch and, when it detects a low logic level corresponding to the closure of the switch, activity of the elbow 7, and the extension direction, interrupts the operation, and awaits the release of the control before restoring control to the patient.

The current measurer 15 arranges for a voltage signal to be associated linearly with an intensity of current absorbed. It is thus possible, by means of an ADC-port channel of the processor 10, to monitor the current absorbed by the drive means and to deactivate them in the event of overload. Tests carried out by the applicant have identified as preferred current measurers 15 integrated circuits of the known types MAX471 and MAX472 which can measure currents up to about 3 A end voltages between about 3V and 36V. Naturally, devices other than those mentioned above may be used, without thereby departing from the scope and objects of the present invention.

The electromyographic signal-transmission means 16 are connected between an ADC port of the processor and the skin electrodes 4 of the functional prosthesis 1 and enable any interference due to supply fluctuations or to electromagnetic waves present in the environment to be filtered from the signal arriving so that the system maintains its normal operative capability even in such environmental conditions.

In a particular embodiment of the present invention, in order to limit noise and to match the impedance of the line of the skin electrodes to those of the ADC, the transmission means 16 comprise, for example, but not exclusively, an RC filter. The use of capacitors has the purposes of attenuating the high-frequency components of any environmental interference.

The serial port is use to interface the integrated port of the processor which produces TTL levels and for connection to an external processor, for example, but not exclusively, my means of a serial port. In order to render the TTL signals of the integrated port, which are of the 0 V type for a low signal and of the+V type for a high signal, compatible with the RS232 standard adopted in a UART port of known type of an external processor (for example, automated baud-rate generation, bit sequencing, reception with election mechanism), the control element 2 comprises an additional RS232 driver circuit of known type.

The expansion connectors 18 is used if the control element 2 has to be connected to additional drive means and/or to sensing peripherals which permit development and modular expansion of the operating and control system. A particular application of this expansion connector 18 relates to a programming method known as "in-circuit" programming. This method enables programming signals to be taken from a dedicated programming card and transferred to the processor without moving the latter form its seat. A particular embodiment of the control element 2 of the present invention comprises an SMD version of the MCU which offers many advantages from the points of view of space occupied and of heat dissipation but has pine of a size and shape such as to make it impossible to remove the processor during the programming stage. With the use of a dedicated external programming card connected to the expansion connector 18, it is thus possible to program the processor without encountering the problems mentioned above.

The control element 2 also comprises indicator means, for example, but not exclusively, LED visual indicators 20 or acoustic indicators, to permit a first quick diagnosis of the operation of the processor.

The negative terminal of the battery 3 is used as a reference potential and the earth of the electronic circuit and the power earth of the drive means of the functional prosthesis 1 are connected thereto. Two supply lines L1, L2 branch out from the positive terminal of the battery 3 for the processor 10 and for the drive means of the functional prosthesis 1, respectively. The line L1 extends through a voltage regulator 21 of known type, for example, but in non-limiting manner, a LM78L05ACZ component which withstands a maximum current of 100 mA and which, together with a capacitor, enables the voltage supplied by the battery to be brought to TTL-compatible levels and the voltage to be stabilized so as to prevent dangerous variations in the supply to the processor 10. The supply line L2 is a power line dedicated to the direct-current drive means of the functional prosthesis and can provide, for example, up to a peak current of 3 A. The line L2, which is not stabilized and is kept at a voltage of 7.5V, is monitored by means of a current-measuring element 31 which causes a wholly negligible maximum drop in the line L2, for example, of about 60 mV.

The control element 2 also comprises a motor brake element, for example, but not exclusively, of electronic type, for keeping the various drive means in position in the absence of stimuli from the skin electrodes. Unlike known control and monitoring systems for electromechanical elbows, in which the brake element was implemented by purely mechanical or electrical elements, in an embodiment of the present invention, the brake element is implemented by producing a low logic level at both of the control inputs of the driver circuit means and short-circuiting the motor by means of the H-shaped bridge. A mechanical reduction element disposed between the motor and the actuator element of the portion of the functional prosthesis concerned enables an electrical feedback lock to be triggered by the generation also of a small back electromotive force. This characteristic renders the electronic brake of the present invention more effective.

In use, a functional device for the disabled with energy from outside the body allows for a series of procedures which regulate its operation, that is: at least one procedure for controlling operation and one or more procedures for the protection and use of the device itself. The control procedure relates to the functions which are directly under the patient's control and are devoted to providing him with a method of operating the drive means of the functional device. This procedure seeks to satisfy most of the patient's requirements both from the point of view of his physiology, for example, muscle-control capability, coordination, and muscle tone, and from the point of view of personal preference such as, for example, greater intuitiveness of one method in comparison with another. The procedures for protection and use, on the other hand, have the character of internal management and safety procedures and are not under the patient's direct control but are devoted to providing support and safety functions. In this case also, the object is to find a good compromise between management efficiency and the degree of freedom which the patient is allowed.

Owing to the large number of functions performed by a functional device for the disabled, a control element of the device generally has to be able to control a plurality of drive means. In order to achieve direct control, as with a natural anatomical part, it would be necessary to assign two muscle signals to each drive means so as to be able to operate it in the two opposite directions by using two distinct muscles as antagonists. Sometimes, it is not possible to adopt this solution because of the physical state of the patient in whom it would be difficult or even impossible to isolate a plurality of distinct and easily controllable muscles. In addition, a large number of input-signal and output-signal channels of the processor could make its design and normal operation complex.

To overcome this problem, an embodiment of the present invention comprises a cyclical selection procedure comprising a step for the identification of two electromyographic signal sources, that is, two distinct muscles easily identifiable by the patient, which are given the role of generic antagonistic controls, a step for the identification of a third electromyographic signal source to which to give the selection-signal role and, finally, a step for the selection of a predefined sequence for selecting the drive means of the functional device for the disabled.

For example, with the use of a functional device such as that described in the present application, comprising a functionally active upper-limb prosthesis 1, it is possible to select a predefined selection sequence comprising, in order, the drive means for the opening/closure of the hand 5, the drive means for the pronation/supination of the wrist 6 and, finally, the drive means for the flexion/extension of the elbow 7. The contraction of one of the two muscles amongst those selected as generic antagonist controls operates the currently-selected drive means in one of the two directions of rotation, for example, opens or closes the hand 5. Contraction of the muscle selected for the selection signal advances the selection in accordance with the sequence described above. When the last drive means is reached in accordance with the sequence established, a further selection command brings about return to the first selection in accordance with the sequence established, thus achieving a cyclical selection procedure. The direction of movement through the functions may also be encoded in the selection command; a weak or short contraction may indicate a change to the next function; a strong or longer contraction may indicate a return to the previous function.

Two different methods may be used for the activation of the selection mechanisms, according to personal requirements and/or the patient's degree of muscular efficiency and coordination capability.

The first method comprises the fitting of an electromyography electrode 4 dedicated exclusively to the function of selection in the predefined sequence. Each time the electrode 4 is stimulated for a predetermined period of time, the drive means are stopped and the control of the prosthesis 1 by the patient is suspended until the selection signal and any control signals for the drive means are relaxed. This step has the purpose of preventing any immediate modification of the drive means with the direction set for the previous selection kept active, leading to undesired actions due to imperfect coordination. On the contrary, with the above-mentioned method, the patient is forced to bring his muscles into an inactive range before regaining control of the prosthesis 1 and thus going on from a known starting stage in which all of the drive means are deactivated.

One of the main advantages of this method is the ease with which the patient can associate the selection function with a single muscle and always with that muscle, and can produce a stable and strong signal which ensures the desired selection, The second method provides for the use solely of the electromyography electrodes 4 dedicated to the generic antagonistic control function. The selection signal is therefore associated with a combination of signals coming from the electrodes 4 for controlling the drive means. For example, successive selections are achieved in the predefined sequence by simultaneously contracting the two muscles for controlling the drive means for a predetermined period of time. In this case also, the above-described sequences are used in the transfer of control to prevent unexpected and involuntary activations.

The main advantage of this method is that the presence of just two muscles in good condition suffices to control all of the operations of the functional prosthesis.

Both of the methods may comprise a further electromyographic-signal width-modulation step (PWM) which enables the intensity of the muscular contraction to be associated with the operative speed of the drive means.

A further embodiment of the present invention comprises a method for the control of the operation of the functional prosthesis which is particularly suitable for patients who have a larger number of signal sources, for example, in the case of electromyographic electrodes, a larger number of available muscles, as well as better coordination of their use. This method of operation comprises a step for the unequivocal assignation of commands to drive means with the use of a plurality of electromyography signals, for example four signals. In the case of an upper-limb functional prosthesis, for example, one electrode is associated with the hand 5, one with the wrist 6, and two with the elbow 7, the command being identified on the basis of its provenance and of the strength of contraction of the respective muscle. The electrode associated with the hand 5 can be selected directly without any preliminary selection and the operative direction of the drive means is determined on the basis of the strength of the electromyographic signal, divided into two distinct periods each associated with a different direction, alternating with periods of inactivity associated with stoppage of the drive means. A similar method is adopted for the wrist 6. The electrodes associated with the elbow 7, on the other hand, perform a normal antagonistic function as described above for the determination of the operative direction of the respective drive means.

The main advantage of this method consists of much more direct and natural control of all of the functions of the functional prosthesis, ensuring a manoeuvrability and speed of execution precluded by the cyclical method.

The system thus permits directly individualized provision of the type of control most suitable for the patient.

A further embodiment of the present invention comprises a method of controlling the operation of the functional prosthesis which is particularly suitable for patients who have only one signal source. In this case, the operative direction of the drive means is determined on the basis of tho strength of the signal, divided into two distinct periods each associated with a different direction, alternating with periods of inactivity associated with stoppage of the drive means.

The procedure for the protection and use of the device of the present invention comprises safety functions such as checking for current-overload and the reaching of the travel limit, and support functions such as the selection of a reference function with programmable pause, an encoding of signals by warning-light means, and an automatic checking procedure.

In some operative situations, the drive means of a functional prosthesis may be subjected to excessive forces above their specification. This problem may lead to damage and wear of the drive means and/or of the circuitry, resulting in a need for repair, in expense, and in a wastage of time, not counting the patient's loss of faith in the use of a functional device for the disabled.

To overcome these problems, the present invention comprises a current-overload monitoring procedure which is performed periodically. The procedure comprises a step in which the current is monitored for a predetermined period of time and a step in which the values detected are analyzed in comparison with pre-set specifications. If the values detected are greater than those specified, the MCU deactivates the drive means by applying, for example, an electronic brake and excluding the patient from control until the muscle which was operating the overloaded drive means has relaxed. The need to detect any overload for a predetermined period of time is due to the normal operation of drive means such as, for example, direct-current motors, which tend to produce an abrupt rise in electrical-current consumption for a short period each time they are activated, especially if they are under load. This procedure, together with the use of an electronic brake, considerably reduces wear of the mechanical and electronic power components, giving the functional device of the present invention greater reliability and a longer life.

The present invention also comprises a procedure for monitoring the reaching of the travel limit, for example, but not exclusively, in the case of an upper-limb functional prosthesis 1, the reaching of the travel limit during the extension movement of the elbow 7. This procedure comprises a step for detecting the activation of the function of the elbow 7, a step for detecting the direction of movement of the elbow 7, a step for detecting the travel-limit detection signal 14, and a step for analyzing the signals detected. When signals relating co the operation of the elbow, to the extension movement, arid to the reaching of the travel limit are detected simultaneously, the processor stops the elbow drive means and removes control of the prosthesis from the patient until he relaxes the respective control muscles. From this situation, the patient can choose to flex the elbow 7 of the prosthesis 1, deactivating the travel-limit detector, or to change drive means within the predefined sequence.

During the everyday use of a functional device for the disabled with a cyclical selection procedure, if the time elapsing between one action and another is greater than ten-fifteen minutes, it is not easy for the patient to remember which was the last drive means selected and it is therefore necessary to activate a test command in order co check this. In the case, for example, but not exclusively, of an upper-limb prosthesis with which the patient is carrying an object and in which the selection relates to the hand, this may lead to disagreeable disadvantages such as loss of grip on the object carried, if an opening movement is brought about, or damage to the object, if a closure movement is brought about.

To overcome this problem, the present invention comprises a procedure for the selection of a reference function, comprising a waiting step in which the period of inactivity of the prosthesis is measured and an automatic updating step which, when a predetermined period of time has elapsed, automatically updates the selected function to a function preselected as the reference function. The patient thus knows that, if a certain period of time has passed without the prosthesis having been operated, the function preselected at that moment is the one selected by him as the basic function and that he does not have to perform any test activation movement.

To prevent the prosthesis being left in a particularly unnatural position, for example but in non-limiting manner, a wrist rotated outwardly through 270°, a particular function may be enabled, which returns the wrist automatically to a neutral position by small movements during periods of inactivity of the prosthesis.

A particular characteristic of the system consists of the ability to manage sensors of different types in order to enable patients with different residual functions to control the prosthesis. For example, but in non-limiting manner, the system may be interfaced with conventional surface electromyography electrodes, with push-button digital sensors, and with analog sensors based on FSR (force sensor resistor) elements.

In a particular embodiment of the present invention, the system comprises a single signal-detection means connected to the control means, for acquiring and transmitting one or more signals for the control of functional devices for the disabled.

In order to be able to perform a diagnostic operation on the state of a functional device for the disabled according to the present invention, the device may be connected to an external processor by means of the data-communication devices described above. If this interfacing is not available, the device of the present invention also allows for a procedure for detecting the operative state of the control element. With the use of the indicator means 20 described above, it is possible to indicate the direction of activation of a drive means, the activation of a procedure for communication with an external processor, a stoppage condition due to overload or the reaching a travel limit, or other similar situations.

The automatic checking procedure enables a predetermined sequence of movements of the functional device to be repeated automatically a predetermined number of times without supervision by the patient. During this procedure, the current-overload control is always active so as to be able to stop the control and put the processor in a state of inactivity in the event of damage or malfunction.

This procedure is particularly advantageous if it is desired to check the resistance of the components of the functional device to stress, or, after a repair, to check its success or even for showing up malfunction which arise in a condition of stress, for example, overheating with a change in the tolerances of the components due to temperature, The integration of all of the functions, the methods, and the procedures described up to now for the operation and control of an upper-limb functional prosthesis for the disabled with energy from outside the body according to the present invention will be described below with particular reference now to FIGS. 3a and 3b.

The first three steps illustrated in FIG. 3a relate, respectively, to initialization, awaiting and controlling a communication, and configuration of the device, and are performed only once within the method and therefore remain excluded from subsequent steps until the arrival of a reset command of any type.

During the "INIT" step, reference values are assigned to the system variables and control bits are set in the dedicated registers of the integrated peripherals. For this reason, unless there are changes in the states assigned to the peripherals, the majority of the values set are not modified further and this step is not performed again. The next step controls communication towards an external processor for checking and modifying the configuration of the control and monitoring system, checking for the presence of a communication and, if detected, conducting it until the cessation of the communication step. Finally, during the last of these three steps, the configuration acquired is transferred to the control variables so as to apply the parameters set.

The next steps of the method form part of the cyclical operation mode and can be divided into two mutually exclusive sets of boxes of which only one will be executed, on the basis of the mode selected. The first block, shown in FIG. 3a, implements the two cyclical modes of operation, that is, the mode of operation with a selection electrode and the combined contraction mode of operation, whereas the second block, shown in FIG. 3b, implements a dual-control mode.

The cyclical mode of operation comprises a first step for updating the inactivity timing and the pause control so as to set the reference function automatically if the prosthesis is left inactive for more than a predetermined period of time. The "mode selection" step then provides for the direction of the process flow to be set, in this case, towards the cyclical function branch. According to the mode selected, a reading of the ADC is performed and any selection is managed in accordance with the mode set. During the next step, the activity of the control electrodes is checked. If there is a negative response, the drive means are stopped and, at the same time, the electronic brake is applied thereto and the cycle is concluded by the return of the flow to the updating of the inactivity timing. If, on the other hand, activity is detected, the operation of the drive means is then managed. First of all, the amount of current absorbed is measured and, if it is found to be excessive for the drive means in use, leads to immediate stoppage whilst awaiting the relaxation of the muscle, and to conclusion of the cycle. If the current is not excessive, the direction is checked and transmitted to the drive means by a comparison between the values detected in the two control electrodes.

The procedure for checking the travel-limit condition then starts. If there is a positive response, the drive means stop and the cycle is interrupted and restarted from the beginning; otherwise discrimination takes place between operation of the elbow or wrist, or of the hand, controlled in PWM. Upon completion of this step, the procedure returns to the updating and to the control of the inactivity timing.

With regard to the dual-control operating procedure, once the three initialization steps described above have been performed, the main flow is abandoned once and for all and execution is transferred to the second block. It can be seen that, in this mode, the inactivity-timing function is excluded, but it will be understood that it is wholly unnecessary in dual-control mode since selection takes place directly on the basis of the muscle contraction performed, without the need to separate the preliminary selection operation. The initial step of the dual-control cycle is that of reading the ADCs and of checking for current overload. The activation of the electrodes relating to the elbow is then checked and, it the result is affirmative, the next step controls the elbow without checking the activation of the hand and wrist electrodes. A priority mechanism for the operation of the elbow relative to the hand and the wrist is in fact thus created. During the elbow-control stage, the hand and wrist drive means are stopped so that several portions cannot be active simultaneously. Finally, the travel-limit and direction checks are performed and the elbow drive means are operated if necessary so as to conclude the cycle.

If the elbow controls are inert, the contraction-strength bands are determined and the band in which the strength of the electromyography signal of the most stimulated electrode lies is identified. Four situations may thus arise.

1) If the signal is in band one, this means that the electromyographic signal is in a band of inactivity and the drive means are thus stopped.

2) If the signal is in band two, three situations that are applicable to the signal which is in this band may arise. It may be a signal passing through this band but directed towards higher bands, it may be a signal returning to this band from higher bands, or it may be a signal intended to belong to this band. The discriminating factor is represented by the rate of change of the signal and by an indicator element which indicates that the signal has reached the higher band. If the rate is high and the higher-band indicator is negative, it is probably a signal in transit and the cycle is thus suspended and a new evaluation is awaited to establish whether the signal has stayed in this band or has left it. If the rate is low and the indicator is negative, it is assumed that the signal is in this band and the system proceeds, for example, to control opening of the hand, or pronation of the wrist, according to which of the two electrodes is most stimulated. If the indicator is positive, irrespective of the rate of change, no action is taken since it is not possible to change the selection until the signal has returned to the previous band, that is, the inactivity band.

3) If the signal is in band three, this is a second inactivity band for enabling the patient to identify the dividing point between the lower band and the upper band more easily and thus to discriminate between the two directions of rotation of the motors.

4) If the signal is in band four, the signal is clearly assumed to be intended for this band and supination of the wrist or closure of the hand is brought about, as appropriate.

Upon completion of the processing of the signal of each band, the program returns to the start of the dual-control cycle so as to be able to identify the location of the signal again.

As shown schematically in FIG. 4 and as described above, in a functional device for the disabled according to the present invention, it is possible to perform monitoring, diagnostic, and calibration operations by means of an external processor with the use of the data-communication means included in the control element. This procedure comprises the provision of an external electronic processor, for example, but in non-limiting manner, a personal computer (PC) 30, of control and monitoring software in the PC, and of means 31 for interfacing between the PC 30 and the communication means of the functional device. A first step enables the operative parameters of the processor of the control element 2 to be acquired in the PC 30, a subsequent step enables these parameters to be displayed and processed in the PC 30, and a last step provides for any modified parameters to the sent to the processor in order to optimize operation or to resolve malfunctions of the functional device. It is thins possible to check the state of the device periodically, for example, to check the state of the batteries, the condition of the cosmetic sheath in the case of an upper-limb prosthesis, to check the sensors and their calibration, to perform an analysis of the electromyographic signal, to check the wear and the state of the mechanical components in the case of an electronic carriage, and to perform a calibration or modification of the operation of the functional device by changing some parameters.

In a particular embodiment of the monitoring system of the present invention, the above-mentioned procedures for the control and monitoring of the device also comprise a step for the provision of remote communication means so as to render the locations of the functional device and of a skilled technician controlling its operation independent of one another.

As shown schematically in FIG. 5, a functional device for the disabled according to the present invention may be connected in the manner described above, to data-communication means, for example, but in non-limiting manner, to an ISDN telephone lane 32 and video communication apparatus 35, so as to be in remote communication with a PC 33. Naturally, data-communication channels other than an ISDN telephone line such as, for example, a normal telephone line, an ADSL line, or a satellite channel may be considered, according to the quality and quantity of data to be transmitted.

A skilled technician in a remote location with a remote PC 33 will be able to share the application software present on the PC 30 connected to the functional device as if it were connected directly to his terminal and to complete all of the above-described monitoring and control operations.

A further embodiment of the monitoring system of the present invention comprises the provision of audio/visual communication means alongside the data-communication means. Many tests carried out by the applicant have in fact shown the importance of audio/visual contact between a patient and the skilled technician in order to achieve and improve correct prosthetic treatment.

The remote monitoring system of the present invention therefore comprises audio/visual communication means, for example, but not exclusively, video cameras connected to a PC, video telephones and video-conferencing devices and/or a PC, both at the patient's home and at the centre for servicing the functional device. The main advantage of this solution consists in the correct timing achieved between the data sent/received by the prosthesis (or carriage) and the audio/visual signal.

In the case of an electronic carriage, for example, it is possible to solve some problems directly at the patient's home and, at the same time, to offer a plurality of services which enables its use to be improved and managed. If a breakdown is identified by a remote connection, the patient can send to the service centre solely the defective element, rather than having to send the entire functional device. For example, the control programs may be modified to render the control more suitable for an initial patient-training stage, by bringing the speed and acceleration parameters to values lower than the standard values. At a subsequent time, when the patient has become more confident, it will be possible to reset values which offer improved performance.

The above-described communication means thus enable a direct and very effective interaction to be achieved between patient and skilled technician which, in some cases, may even allow the training stages of the functional device of the present invention to be performed remotely.

Naturally, the principle of the invention remaining the same, the forms of embodiment and details of construction may be varied widely with respect to those described, without thereby departing from the scope of the present invention.

What is claimed is:

1. A method for the control of a functional device for the disabled with energy from outside the body, comprising the step of providing a control and monitoring system comprising control means connected to sensor means and to actuator means which can operate drive means of the functional devices for the disabled in use, characterized in that it further comprises the following steps:

a) selecting at least one electrical-signal source and associating it with a sensor element,
   b) associating at least one sensor element with each of the actuator means,
   c) defining at least two ranges of electrical-signal strength,
   d) assigning to each range a respective signal for the activation and/or selection of the actuator means,
   e) detecting an electrical signal coming from the sensor element and comparing it with the at least two pre-defined ranges, and
   f) generating the corresponding signal for the activation and/or selection of the actuator means.

2. A method according to claim 1, characterized in that it comprises the following steps:

(a) predefining at least one neutral position of the functional device for the disabled,
   (b) predefining at least one limit position of the functional device for the disabled,
   (c) detecting at least one limit position by a check of the actuator means,
   (d) detecting the absence of activation signals for a predetermined period of time, and
   (e) activating the actuator means in order to bring the functional device for the disabled from the limit position to the neutral position.

3. A method according to claim 1, characterized in that is comprises the following steps:

(a) detecting the current supplied to a drive means by a supply for a predetermined period of time,
   (b) analyzing the values detected by comparing them with predetermined values, (c) deactivating the drive means if the values detected are above the predetermined values, and (d) repeating step a) after the predetermined period of time.

4. A method according to claim 1, characterized in that it comprises the following steps:
   (a) providing a functional device for the disabled, comprising at least one drive means operable in two preferential directions corresponding to two distinct activation signals,
   (b) detecting the presence of a signal for the activation of at least one drive means and detecting its direction of operation by a comparison of the activation signals,
   (c) detecting the presence of a travel-limit signal relating to the drive means,
   (d) deactivating the drive means, and
   (e) keeping the drive means deactivated until the absence of the travel-limit signal or the absence of any signal for the activation of the drive means is detected.

5. A method according to claim 1, characterized in that it comprises the following steps:
   (a) providing a control and monitoring system comprising data-transmission means connected to the control means,
   (b) providing data-processing means outside the system,
   (c) connecting the data-processing means to the data-transmission means of the control and monitoring system, and
   (d) activating an exchange of data between the data-processing means and the control means.

6. A method according to claim 5, characterized in that the data-processing means and the control means are connected by means for the remote transmission of audiovisual and/or data signals.

7. A system for the control and monitoring of functional devices for the disabled with energy from outside the body according to claim 1, comprising, in combination, actuator means which can be connected to drive means of a functional device for the disabled in use, data-processing means, and control means connected to the actuator means and to the processing means, characterized in that it comprises a single signal-detection means connected to the control means, for acquiring and transmitting one or more signals for the control of functional devices for the disabled.

8. A system according to claim 7, characterized in that the signal-detection means are selected from within a group of sensors comprising: surface electromyography electrodes, push-button digital sensors, and analog force sensors.

9. A system according to claim 8, characterized in that data-transmission means are connected to the processing means in order to transmit and/or to receive data remotely.

10. A system according to claim 9, characterized in that the control means further comprise an electronic motor brake element.

11. A system according to claim 10, characterized in that it comprises at least one data-storage element and one or more microprocessors (10) connected to electronic power circuits (11, 12, 13) for the operation and control of direct-current motors of the functional device, and to one or more filters with capacitors for filtering the one or more signals coming from the sensor element.

12. A method for the control of functional devices for the disabled with energy from outside the body, comprising the step of providing a control and monitoring system comprising control means connected to sensor means and to actuator means which can operate drive means of the functional devices for the disabled in use, characterized in that it further comprises the following steps:
   a) selecting at least one pair of signal sources for the generation of two antagonistic signals for the activation of the actuator means,
   b) providing a predefined cyclical sequence of signals for the activation of respective actuator means,
   c) associating a selection signal with the simultaneous generation of two antagonistic signals of the at least one pair of sources identified,
   d) selecting one of the activation signals within the cyclical sequence by the generation of the selection signal, and
   e) selectively activating the actuator means corresponding to the activation signal selected by the generation of one of the two antagonistic signals for the activation actuator means.

13. A method according to claim 12, characterized in that it comprise the step of:
   a) identifying a third signal source as the source of a selection signal.

14. A method according to claim 13, characterized in that it further comprises the following steps:
   a) selecting a preferred activation signal, within the predefined cyclical sequence of activation signals,
   b) detecting the absence of activation signals for a predetermined period of time, and
   c) selecting the preferred activation signal within the predefined cyclical sequence when the predetermined period of time has elapsed.

* * * * *